US012239883B2

(12) United States Patent
Kinnunen

(10) Patent No.: US 12,239,883 B2
(45) Date of Patent: Mar. 4, 2025

(54) METHOD FOR OPTIMIZING TRAINING BASED ON BODY TEMPERATURE VARIATIONS

(71) Applicant: Oura Health Oy, Oulu (FI)

(72) Inventor: Hannu Kinnunen, Oulu (FI)

(73) Assignee: Oura Health Oy, Oulu (FI)

( * ) Notice: Subject to any disclaimer, the term of this patent is extended or adjusted under 35 U.S.C. 154(b) by 968 days.

(21) Appl. No.: 17/317,159

(22) Filed: May 11, 2021

(65) Prior Publication Data

US 2021/0354001 A1    Nov. 18, 2021

(30) Foreign Application Priority Data

May 12, 2020  (FI) ..................................... 20205472

(51) Int. Cl.
| | | |
|---|---|---|
| *A63B 24/00* | (2006.01) | |
| *G01K 1/14* | (2021.01) | |
| *G16H 10/60* | (2018.01) | |
| *G16H 20/30* | (2018.01) | |
| *G16H 40/67* | (2018.01) | |
| *G16H 50/30* | (2018.01) | |

(Continued)

(52) U.S. Cl.
CPC ............ *A63B 24/0075* (2013.01); *G01K 1/14* (2013.01); *G16H 10/60* (2018.01); *G16H 20/30* (2018.01); *G16H 40/67* (2018.01); *G16H 50/30* (2018.01); *G16H 50/70* (2018.01); *A63B 2220/836* (2013.01); *A63B 2230/505* (2013.01); *G16H 50/20* (2018.01)

(58) Field of Classification Search
CPC ..... A63B 24/0075; G16H 10/60; G16H 40/67
See application file for complete search history.

(56) References Cited

U.S. PATENT DOCUMENTS

| 10,335,060 B1* | 7/2019 | Kahn .................. A61B 5/7246 |
| 2004/0133081 A1 | 7/2004 | Teller et al. |

(Continued)

FOREIGN PATENT DOCUMENTS

| CN | 207822470 U | 9/2018 |
| JP | 2016087170 A | 5/2016 |

(Continued)

OTHER PUBLICATIONS

BMC Women's Health; Nocturnal finger skin temperature in menstrual cycle tracking; (2019).

(Continued)

*Primary Examiner* — David L Lewis
*Assistant Examiner* — Shauna-Kay Hall
(74) *Attorney, Agent, or Firm* — Holland & Hart LLP

(57) ABSTRACT

The present disclosure introduces a method for providing substantially optimal training instructions to a user based on temperature measurements performed by a wearable device. The algorithm determines non-REM sleep phases of the user, measures the maximum temperature of the NREM sleep phase or an averaged value among the maximum values of several NREM sleep phases in a night, and it determines most appropriate training instructions for the user based on that temperature information. Gender and age may also have an effect in the training instruction determinations. Training information and alerts can be given via a smartphone application to the user.

18 Claims, 14 Drawing Sheets

(51) Int. Cl.
*G16H 50/70* (2018.01)
*G16H 50/20* (2018.01)

(56) References Cited

U.S. PATENT DOCUMENTS

| | | | | |
|---|---|---|---|---|
| 2007/0027404 | A1* | 2/2007 | Saini | A61B 10/0012 |
| | | | | 600/551 |
| 2014/0310019 | A1* | 10/2014 | Blander | G16H 40/67 |
| | | | | 705/2 |
| 2015/0199494 | A1* | 7/2015 | Koduri | G16H 20/30 |
| | | | | 700/91 |
| 2016/0220867 | A1* | 8/2016 | Flaherty | G16H 20/30 |
| 2017/0007214 | A1 | 1/2017 | Dillen | |
| 2018/0256078 | A1* | 9/2018 | Vaterlaus | A61B 5/7435 |
| 2019/0371449 | A1* | 12/2019 | Rindal | G16H 20/30 |

FOREIGN PATENT DOCUMENTS

| | | |
|---|---|---|
| WO | 2016135382 A1 | 9/2016 |
| WO | 2018226885 A1 | 12/2018 |

OTHER PUBLICATIONS

Lorrain Conwell; Perpetua Crossfit & SWEAT Coach; Exercise and Your Period; (Apr. 27, 2020).
REM vs. Non-REM Sleep (https://www.livescience.com/59782-stages-of-sleep.html).
European Search Report; Appl. No. 21172825.8 (Jun. 10, 2021).
Finnish Patent and Registration Office Search Report—Application No. 20205472; Dated Nov. 20, 2020.

* cited by examiner

| Temperature | Training amount (female) | Training amount (male) |
|---|---|---|
| High | Max 50% | Max 75% |
| Middle | Max 90% | Max 100% |
| Low | Max 125% | Max 125% |

Figure 4

METHOD FOR OPTIMIZING TRAINING BASED ON BODY TEMPERATURE VARIATIONS

CROSS REFERENCES

This application claims the benefit of Finland Patent Application No. 2020-5472, filed on May 12, 2020, which is hereby incorporated by reference in its entirety into this application.

TECHNICAL FIELD

The present disclosure relates generally to optimization and personalization of training and rest guidance for a user based on the skin temperature and its variation cycles within the users.

BACKGROUND

There are different kinds of activity and training monitors which can measure user's heart rate, heart rate variability and motions or activity. Training applications may make a training program or the training program can be received from a personal trainer and it can be loaded to a wearable device. A typical training program consists of a number of training sessions per week and each session can be instructed for example based on a suitable heart rate range, for example 130-150 beats per minute for 40 minutes, or being an amount of activity for example of 10 kilometers or 10,000 steps, or a high-power activity for 50 minutes. Training advice for a gym can be similar or it may comprise different weights, repetitions and muscle groups, or certain movements or instructions to use certain gym training devices.

Training generally improves person's health and performance in everyday activities and in professional and recreational sport activities. However, many studies show that the training effect is not similar in all persons, although the training is adapted to person's age and performance level. In some cases, it has been shown that the training effect can be negligible, or in some rare cases even negative. The reasons are not exactly known, but some possible explanations can be a stress level, different hormonal cycles, sleep quality or sleep scores, morningness or eveningness types, food intake, or a temporal illness such as e.g. flu or cough, or unsuitable training program.

Body temperature of a human being is rather stable, in around 37 degrees Celsius. It is known that body temperature varies over the 24-hour cycle, the day and night (circadian variation). The body temperature also elevates during a strenuous exercise. The body temperature is also a natural defensive reaction against inflammation. It elevates during a flu, for example, and during a severe pneumonia. In very severe cases, the temperature can reach 41 or 42 degrees Celsius. There may be many other hormonal, physiological and medical reasons why the body temperature is changing and varying from day to day, week to week. The variations can be cyclic within a day (ultradian variation), weeks or months (seasonal variation) or they can be occasional and temporary, or continuous and repetitive.

It is also well known that the body temperature varies during women's menstrual cycle. After the ovulation the body temperature elevates 0.3-0.8 degrees Celsius. The change is small but it can be detected when following for example morning temperature carefully and continuously every morning.

A menstrual rhythm causes big changes in woman's body. It is known that physical performance is not unaffected due to the menstrual phases. Due to this fact, it is known to give more advanced training guidance during the menstrual phases of women. The web page https://coconutsandkettlebells.com/training-with-your-menstrual-cycle/ for example divides a typical 4 weeks' menstrual cycle to four different weeks. The web page guides to track the user's cycles by taking the BBT (i.e. basal body temperature) each morning at the same time before getting out of bed, with a basal thermometer. And then the user may track her temperature changes from a printable chart. Once the ovulation occurs, the user experiences a rise in her BBT. This rise is typically around 0.5 degrees Celsius, and the temperature shift is sustained until progesterone begins to drop off and menstruation starts over again. The day just before this temperature shift is the day the female user ovulated. Typically, it is marked as a $14^{th}$ day from the beginning of the cycle.

The average menstrual cycle length is 28 days, but most women will vary from this. It can be 23-36 days and still be normal. The cycle length can vary month to month. Sometimes being lighter, sometimes harder.

The menstrual cycle is not the only reason, which affects the body temperature. In addition to progesterone, other hormonal changes can also affect temperature and its control. Also, stress and mental and physical vitality and fatigue can change the body temperature. Negative caloric balance may lead to lower body temperature.

An elevated body temperature may affect physical performance, too. At least high ambient temperature can reduce the maximum performance especially in strenuous and long-lasting endurance sports such as in marathon.

The body temperature is not easy to monitor continuously. An accurate method for defining body temperature is to measure temperature from a rectum or from axilla (i.e. armpit) or from a mouth. A continuous monitoring is not possible from the places mentioned above. Wearable devices can be used to measure the skin temperature but variations are very large due to skin contact variations, skin's thermal conductivity variations, and temperature variations of different body parts even although the (basal) body temperature would be constant. The practical measurements show as large as +/−3 degrees Celsius variations, when the body temperature varies only +/−0.3 degrees Celsius.

During the day, skin temperature is lower than during the night. At night the skin temperature follows and resembles the body temperature to some extent, but it can also vary a lot, especially when measured from the wrist or a finger. Thus, a wearable skin temperature monitoring cannot be used directly to estimate the body temperature. For example, US patent application publication US 2004/133081 discloses a method to measure the skin temperature. Also the PCT application WO 2016/135382 by Oura Health Oy discusses that the skin temperature can be measured by a temperature sensor equipped on a wearable ring.

There is not a reliable solution to optimize and personalize user's training based on the user's body temperature measured by a wearable device from the user's skin.

SUMMARY

Aspects of the present disclosure provide for a ring with a skin temperature sensor, defining skin temperature especially at night time, for forming a temperature cycle over days, possibly defining menstrual cycle for a female user, and giving exercise guidance related to on-line measurements and possible cycle estimation for the following days.

In a first aspect, the disclosure introduces a method for providing instructions (e.g., substantially optimal training instructions) to a user. The method may include collecting a set of information related to the user comprising age and gender; receiving a set of measurement data related to the user comprising a measured skin temperature obtained by a wearable device worn by the user; determining a representative temperature value for at least one time period, where the time period is a pre-selectable parameter; determining a day-to-day temperature cycle based on successive representative temperature values for the at least one time period; and determining training instructions for a current day based on at least a latest temperature value, and a relation of the latest temperature value to the temperature cycle.

In some examples, the time period is selected from values of 12 hours or 24 hours.

In some examples, the relation comprises at least qualitative values of high, middle, and low.

In some examples, the method further comprises measuring the skin temperature of the user by a temperature sensor comprised in the wearable device, wherein the wearable device locates adjacently and in contact or in immediate proximity with the user's skin.

In some examples, the wearable device is a smart ring.

In some examples, the temperature to be measured is measured during a predetermined time period in the night or in the user's sleeping time.

In some examples, the method further comprises determining of the representative temperature value for the at least one time period is performed by selecting a maximum skin temperature within a defined time window during defined sleeping periods, where the maximum skin temperature is an averaged value over a period of 10-30 minutes.

In some examples, the defined sleeping period is NREM sleep, and in case there are multiple NREM sleep periods in the night or in the sleeping time, selecting a median or minimum or maximum value, or an average value of the temperature values of the NREM sleep phases.

To define the above term "NREM", it means the Non-rapid eye movement stage of the sleep or non-REM sleep, which can also be called as quiescent sleep. It consists of sleep stages 1-3 (i.e. stages NREM-1, NREM-2 and NREM-3), and the rapid eye movement (REM) sleep is not included there. The NREM sleep can be interpreted as a more precise definition of the various deep sleep stages, as a single definitive term (such as light sleep or deep sleep). The NREM sleep is characterized by higher and more stable skin temperature, and lower and more stable resting heart rate than in REM sleep.

In some examples, the method further comprises determining of the day-to-day temperature cycle based on representative temperature values for the at least one time period is based on successive temperature values.

In some examples, the method further comprises picking the successive temperature values once a day; and using a moving average of three, four or five previously obtained, successive temperature values.

In some examples, the method further comprises selecting training instructions for the current day based on the latest temperature value obtained either today or yesterday, so that if the latest temperature value is higher than average, the selected training instructions comprise a lower intensity exercise and/or a longer lasting exercise, and if the latest temperature value is lower than average, the selected training instructions comprise a higher intensity exercise and/or a shorter lasting exercise and/or stretching or rest instead of training.

In some examples, the method further comprises in the determination of the day-to-day temperature cycle, the temperature curve is further extrapolated by estimating the temperature for the following days; and using the estimated temperature values for the training instructions and/or for training planning instructions for the future.

In some examples, the method further comprises providing the training instructions comprising an amount of training, a type of training, a duration of training, an intensity of training, a time during the day for the training to take place, and/or a guidance to stretch or rest.

In some examples, the method further comprises giving an alert to the user for a start of the training and/or for receiving the training instructions.

In some examples, the method further comprises measuring activity of the user during a training time and determining if the user has performed the training as instructed.

In some examples, the method further comprises collecting feedback from the user based on the measured activity during the training time and a personal feedback about a feeling during and/or after the training.

In some examples, the method further comprises modifying the training instructions based on the collected feedback from multiple users based on the measured activity during the training time and the personal feedback about the feeling during and/or after the training, and the relation of the related latest temperature value to the temperature cycle.

A system is described for providing training instructions to a user. The system may include a computer, a personal smartphone, and a wearable device worn by the user; wherein the system is configured to collect, by the smartphone, a set of information related to the user comprising age and gender; receive a set of measurement data related to the user comprising a measured skin temperature obtained by the wearable device; determine a representative temperature value for at least one time period, where the time period is a pre-selectable parameter, either in the smartphone or in the computer; determine a day-to-day temperature cycle based on successive representative temperature values for the at least one time period, either in the wearable device, in the smartphone or in the computer; and determine training instructions for a current day based on at least a latest temperature value, and a relation of the latest temperature value to the temperature cycle, either in the smartphone or in the computer.

A computer program product is described for providing training instructions to a user, wherein the computer program product comprises program code, which is executable when run in a processor. The computer program product is configured to execute the steps of collecting a set of information related to the user comprising age and gender; receiving a set of measurement data related to the user comprising a measured skin temperature obtained by a wearable device worn by the user; determining a representative temperature value for at least one time period, where the time period is a pre-selectable parameter; determining a day-to-day temperature cycle based on successive representative temperature values for the at least one time period; and determining training instructions for a current day based on at least a latest temperature value, and a relation of the latest temperature value to the temperature cycle.

BRIEF DESCRIPTION OF THE DRAWINGS

FIG. 4 is an illustration of exemplary training guides in accordance with aspects of the present disclosure.

DETAILED DESCRIPTION

Figure 1:
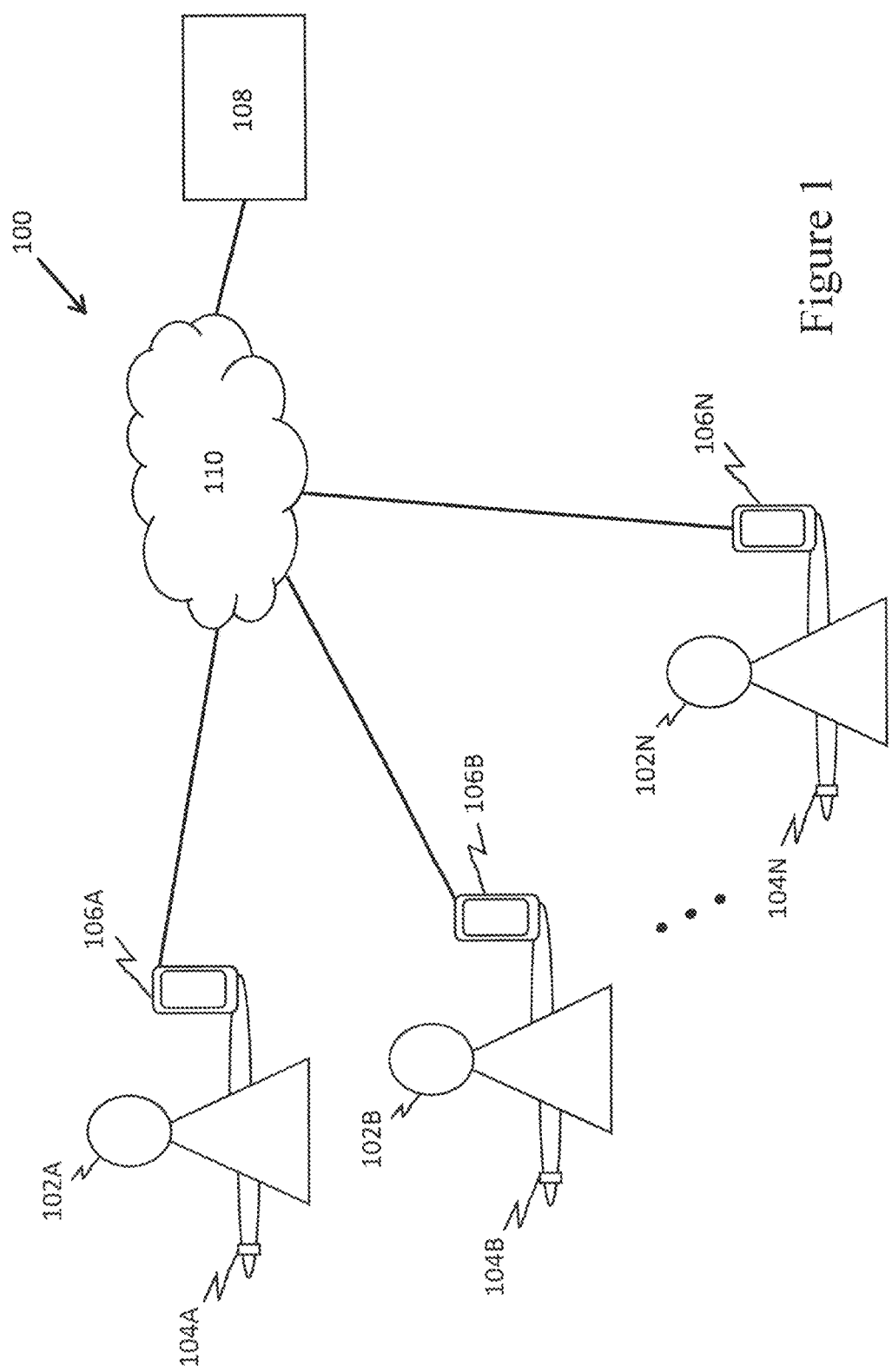
FIG. 1 is a schematic illustration of a system for providing an optimal training guidance based on temperatures measured by a wearable device, in accordance with aspects of the present disclosure.

The following detailed description illustrates various examples and aspects of the present disclosure and ways in which they can be implemented.

The present disclosure provides a method for defining guidance or instructions such as a substantially optimum training method and time for the user.

Existing techniques may be deficient in that they may not be able to define a reliable and correct temperature value from among multiple measured temperature values during the day/night for representing best the user's daily body temperature for the follow-up of the temperature cycles for a user. This may be true especially because the skin temperature varies a lot over the day. For example, the variation can be ten times higher than the actual temperature change of the body temperature which is tried to be evaluated and defined.

Existing techniques may also be deficient in that they may not be able to filter and process single daily temperature values to form a day-to-day temperature cycle. As well as the temperature varies from minute to minute, temperature varies also from day to day. An advanced signal processing algorithm (i.e. method) may be needed to filter and process daily temperatures to define a reliable temperature day-to-day curve. It may be important to define the temperature value for each day so that it is representing the daily temperature value and the defined temperatures can be compared to each other over the days.

Existing techniques may also be deficient in that they may not be able to use the created temperature cycle for providing training instructions to the user for the day. For example, a method of leveraging temperature cycles for providing training instructions has not been considered before. Although the impacts of the menstrual cycle on training has been considered, the wearable assessment of the menstrual cycle and training has not yet been considered.

Existing techniques may also be deficient in that they may not be able to use the created temperature cycle for more detailed training planning to a user. This has not been linked together before either. Based on the temperature cycle and its extension/estimation/forecast for the following days, the training schedule and a single training session can be planned optimally (comprising training intensity, training time, training type or selecting rest).

Furthermore, aspects of the present disclosure also provide for a system (i.e. arrangement or collection of devices or other apparatuses) for defining the substantially optimum training method and time for the user.

First, concerning the definitions of different sleep phases, NREM (i.e. non-REM sleep) is of the particular interest in the present disclosure, and the NREM can be divided in NREM-1, NREM-2 and NREM-3 stages. The real challenge is that skin temperature values are normally the highest during a first tertial ($\frac{1}{3}$) of the sleep where most deep (NREM-3) sleep is, and sleep is predominantly NREM throughout the first tertial anyway. Skin temperature is closest to the core body temperature when the skin temperature has its local maxima. However, instead of the first tertial of the night, it would be desirable to estimate the basal body temperature that usually occurs during the latter tertials of the night, when more REM sleep is found. On the other hand, REM sleep is characterized with lack of temperature control overall. In order to overcome these problems, it would be recommendable to look at periods, when the heart rate (HR) is low and most stable, and the temperature is high and most stable during the two last tertials of sleep, or e.g. between 2 am-7 am. And this choice by definition looks for NREM sleep periods, when skin temperature is most probably the closest to the core body temperature. The second alternative is to transform the HR information into estimated core temperature information—for example assuming that +10 bpm (beats per minute) equals +0.2° C.—and then starting from a big bias, and further reducing bias until any skin temperature value equals to the lowest estimated core temperature value. After that it is acceptable to look for a minimum estimated core temperature value during the morning hours. This is only a single example on how to combine the heart rate and the skin temperature to estimate core body temperature variation. The third option is to simply rely on that any stable local maximal skin temperature, and especially the first, second and third highest ones observed during the night, is likely to be close to the core body temperature, and therefore, they (i.e. one of them) can be used to represent the core body temperature during that night. "Stable" can mean e.g. a constant value within 0.3° C. for at least 15 consecutive minutes. The benefit of the third option is that a value can be obtained for each night, and the resulting error from not getting the representative value from morning hours but rather during any hour of sleep, can be less than how much REM sleep periods or how people place their hands during the night can affect the skin temperature readings.

FIG. 1 illustrates an example of a general arrangement (i.e. a system) 100 according to the present disclosure, which enables providing substantially optimal training instructions (i.e. guidance or scheme) to a user 102. The algorithm is based on user body temperatures measured by a wearable device 104, during the night-time or user's sleeping time, in general. Therefore, the "user" is sometimes equated with the term "sleeper" in this disclosure. The "substantially" optimal means that there can be several quite good and reasonable training schemes for a certain user situation in a certain date, but the present disclosure is not necessarily restricted to select only the absolutely "best" training scheme. It can be also said that if the best training scheme for the user is "100%" satisfactory in the situation, the present disclosure may select e.g. some of the schemes exceeding 90% satisfactory levels or some other predefined threshold. Thus, we have formulated the selection among the training instructions to be "substantially optimal", which means the same as "sufficiently optimal" considering the situation in practice.

In other words, the general system structure is illustrated in FIG. 1, showing a group of users 102 i.e. sleepers (in the same room, or just a general group of different persons each locating anywhere) who are subject to the analysis according to the method according to the present disclosure. In other words, the main concern for the algorithm is a single user 102, but the algorithm may apply data obtained in the history from several users 102A, 102B, 102N, when performing calculations and determinations. The system or arrangement 100 comprises one or more users 102, among which users A, B and N are shown (N means any positive integer, not just fourteen users), as users 102A, 102B and 102N. Each user 102A, 102B, . . . , 102N has a wearable device 104A, 104B, . . . , 104N, which can be also called as a sleep monitoring device, which is an electronic device with at least one sensor. In an example, the wearable device 104 is a wearable, smart ring. In another example, the wearable device 104 is a smart wrist-held device. In yet another example, the wearable device 104 comprises a sensor or a group of sensors placed on top of the human skin in a desired place, or a sensor or a group of sensors placed within a fabric of a cloth worn by the user. In this example, each user 102 also has a personal smartphone 106A, 106B, . . . , 106N, and in a personal sense, this means that a single user which is considered by the training instructions algorithm, has a personal smartphone 106. The smartphones 106 may provide access from the wearable smart devices 104 to the network 110; in other words, the respective smartphone 106 of the user (or a sleeper) act as gateways for the measured personal data by having a connection both to the personal wearable device 104, and to the network 110. The network 110 is represented here with a cloud symbol. As part of the network, there is a server 108 which can be a computer within the user's own premises (e.g. at home) or a computer within service provider's premises. Thus, the wearable devices 104 are all connected to the network 110, for transferring the measurement results from all desired users 102 to the server 108, and for other needed information transfer (such as personal ID information and/or other related information concerning the user(s) and their measurements).

Figure 2:
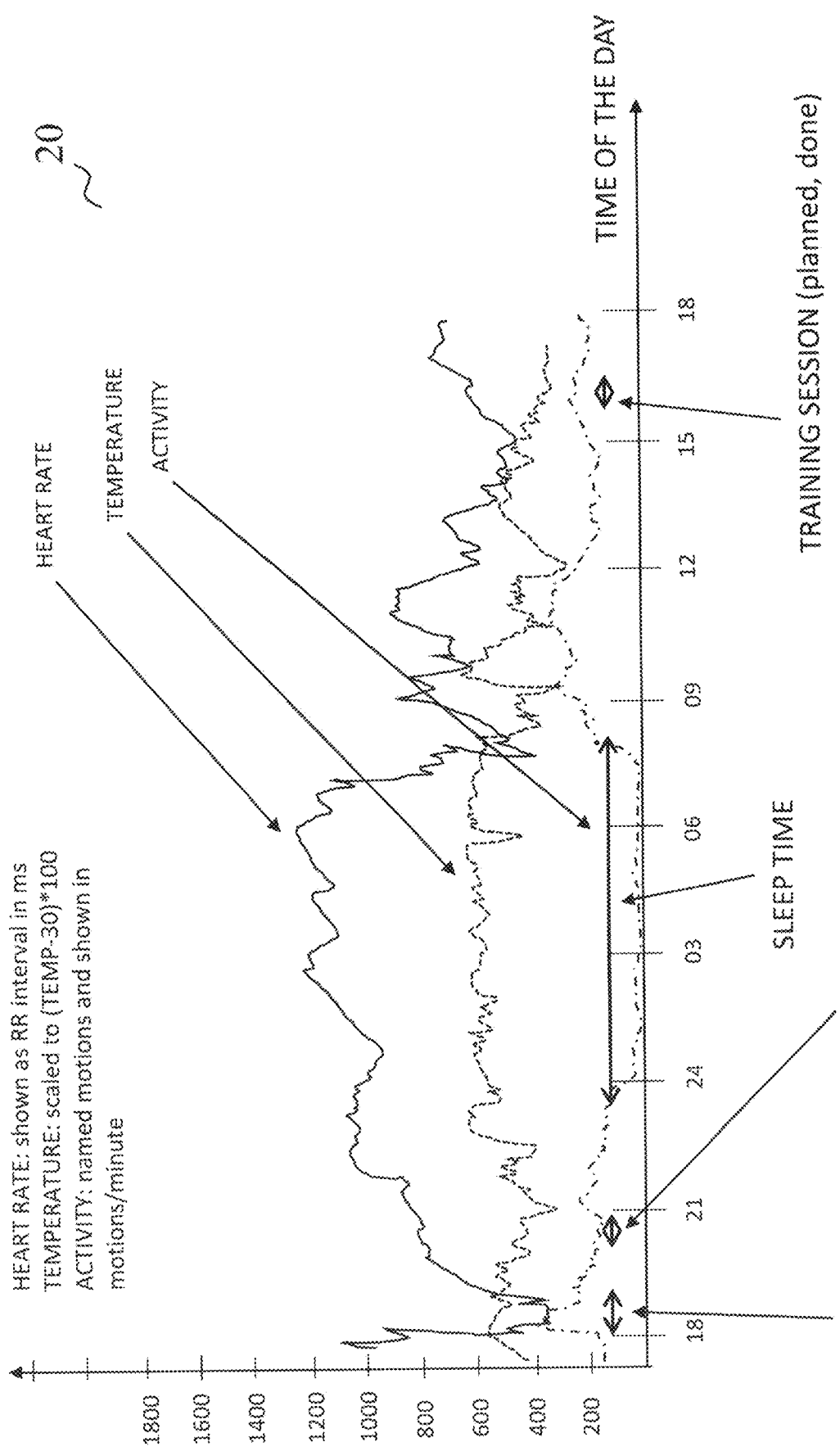
FIG. 2 is an illustration of exemplary measurement data of a person including activity, heart rate and skin temperature, in accordance with aspects of the present disclosure.

FIG. 2 illustrates exemplary measurement data 20 of a user (i.e. a person) comprising activity, heart rate and skin temperature, in an example of the present disclosure. The X-axis shows a clock time of a day, from 18:00 (or 6 PM) of a first day to 18:00 in the next day, as a 24-hours period focusing on night-time activity levels of a sleeping person. The uppermost curve (continuous line) represents heart rate, shown here as heartbeat intervals in milliseconds over the course of a 24-hour period. It can be seen in this example, that the minimum heart rate (i.e. the maximum heart beat interval) occurs at 02:40 AM and 6:00 AM, and the maximum heart rate (i.e. the minimum heart beat interval) occurs between 6-7 PM, when the user has had a training session. The middle curve (dashed line) in FIG. 2 illustrates a temperature of the user, measured in a periphery of a human body. The temperature is scaled here as "(TEMP-30)*100" which results in the majority of the temperature values locating close to "600" (corresponding to 36° C., just below the most normal human core body temperature that is normally 36.5-37.0° C. in the morning hours). During the day-time, the temperature in the periphery deviates more than in the night-time. This happens especially in colder climates during wintertime, when being outdoors performing only light activities such as walking.

The third, lowermost curve (in dot & dashed line) represents user activity. This has been determined as named motions made by the user, which are shown as number of motions per minute. Naturally, during the night-time this value is low, and e.g. during a training session from 6-7 PM, the activity level is high.

The graph also shows a couple of planned training sessions during the 24 hour period, where only the second one has been actually done. At least the activity graph reveals this. Also the sleeping time of the user can be clearly seen as the period of low activity between 24 PM and 7:30 AM.

All the parameters, measured values and times of proposed training sessions are merely exemplary in FIG. 2.

Figure 3:
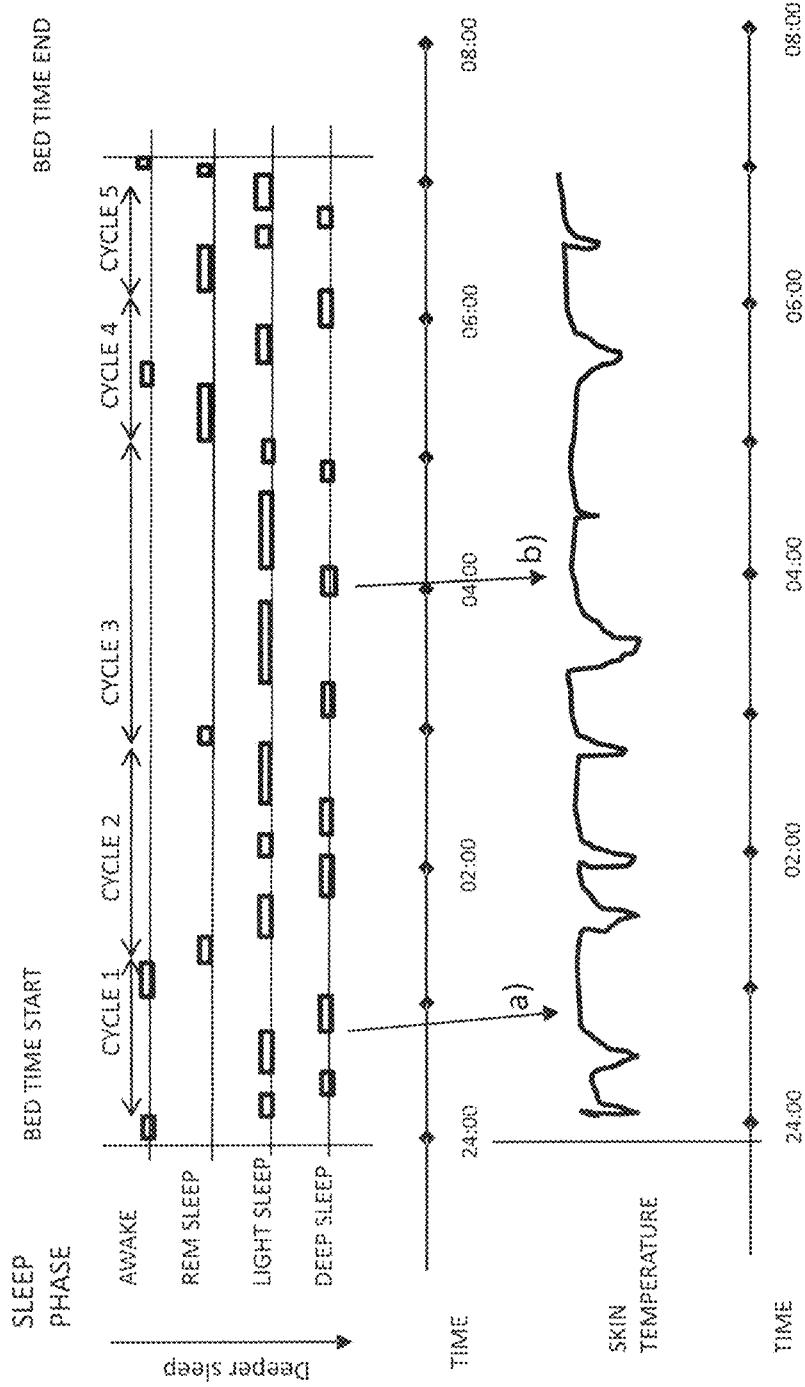
FIG. 3 is an illustration of exemplary measurement data of skin temperature of a person, and determined sleep phases and cycles in accordance with aspects of the present disclosure.

FIG. 3 illustrates sleep phases, sleep cycles and the skin temperature of the user in an exemplary example of the present disclosure. The illustration shows a night-time between 24 PM and 7:15 AM. The classified sleep phases of the user are "Awake", "REM sleep", "Light sleep" and "Deep sleep", which go from lighter forms of sleep (or non-sleep) towards deeper sleeping states. Light sleep and deep sleep are here NREM sleep phases, for instance. Deep sleep is defined to be a sleep type, which has been defined by the sleep researchers and doctors, where the deep phase of the sleep best corrects the damages occurred in the body of the human being during the day. Different sensed sleep phases for the user are marked in this exemplary night as a group of various time ranges in that particular sleep phase. From that data, we may recognize certain sleep cycles. In this example, it is possible to recognize five different sleep cycles within a single night; these are marked as "Cycle 1" to "Cycle 5". It can also be seen that the sleeper reaches nine different time periods of deep sleep, and there are two times in the middle of the night (in the middle of the sleeping) when the user wakes briefly up.

Simple rules can be determined for defining different phases of sleep. These rules can be defined by using measurable characteristics obtained from the sleeping person him-/herself. Such characteristics may involve the skin temperature, activity (i.e. movement) of the sleeper and the heart rate of the sleeper. These parameters are also measurable directly with a sleep monitoring device without a need for additional sensing e.g. elsewhere in the bedroom premises (like in prior art). It is emphasized that the following parameter limits are mere examples, and also some other values and ranges can be applied in determining the sleep phases. In an example, it is possible to tune these parameter values by updating them in the memory which is accessible by the server.

The Awake phase can be determined as follows:
skin temperature T: T<35 (the unit is degrees Celsius: ° C.)
activity A: A>9 (the unit is seconds of user motion per minute)
heart rate HR: HR>65 (the unit is beats per minute, i.e. "bpm")

The REM Sleep can be determined as follows (with same units as in the above):
skin temperature T: T>33
activity A: 2<A<10
heart rate HR: 55<HR<70

The Light Sleep can be determined, correspondingly:
skin temperature T: T>33
activity A: 0<A<3
heart rate HR: 50<HR<65

Finally, the Deep Sleep can be determined to occur within the following parameter ranges:
skin temperature T: T>35
activity A: A<1
heart rate HR: 40<HR<65

In practice, all three conditions can be checked simultaneously or in a serial manner in order to determine the specific sleep phase for the sleeping person. In practice and in the simplest case, the rule can be based even on only one parameter, for example activity, after the earlier sleep phases have been properly defined for the particular sleep period. This uses the order and serial nature between the different sleep phases in the analysis. For example, at first, all three parameters are followed and the first sleep phases have been defined based on the three parameters, but after the first light sleep or deep sleep period, the activity is only followed and the next sleep phases are defined based on the activity count only as the rule says in the above examples.

The lowermost curve (continuous line) of FIG. 3 shows the skin temperature of the user during the night-time. It can be seen from this example, that the skin (periphery) temperature of the user varies and temperature values and changes can be used for a sleep phase defining. During the deep sleep phases the skin temperature is typically higher and stable. The deep sleep phase can be also defined such as a sleep phase with stable and high skin temperature. Also other characteristics like absence or low number of movements and stable, normal-to-low heart rate can be used to define the sleep phase, hence the name "deep sleep" is used here. Marked point a) and b) shows examples of the deep sleep phases with stable and high skin temperatures.

FIG. 4 illustrates an example of a group of possible training guides (i.e. instructions). The training instructions are based here in the measured temperature of the user, and furthermore, the age of the user may have an effect on the given training instructions. In the example of FIG. 4, the temperature measurement curve is taken into account for a predetermined number of consecutive days of the measurement history of this particular user (or even the whole measurement history of this particular user), and it is split into four quartiles based on the temperature values, in an example. These quartiles thus locate on a Y-axis, and they can be defined as 0=the mean temperature between the maximum and the minimum recorded peripheral temperature of the user; +50% being the maximum temperature value, and −50% being the minimum temperature value. Thus, the quartiles are 1)+25 . . . +50%, the uppermost quartile; 2) 0 . . . +25%, the second uppermost quartile; 3) −25%-0, the third uppermost quartile, and 4) −50% . . . −25%, the lowermost quartile. This is of course just an example of the possible values in the present disclosure. Now FIG. 4 defines that the user temperature is "High", if it is in the first quartile i.e. 1). Then it defines that the temperature is "Middle" if it is in the second or third quartiles i.e. 2) or 3). Furthermore, it defines that the temperature is "Low", if it is in the fourth quartile i.e. 4).

Then, the training instructions for a female user or to a male user can be defined as in this example. In case the female user has high temperature, she is instructed to train in max 50% of the average intensity, or max 50% of the average training time. If the male user has high temperature, he is instructed to train in max 75% of the average intensity, or max 75% of the average training time. In case the female user has middle temperature, she is instructed to train in max 90% of the average intensity, or max 90% of the average training time. If the male user has middle temperature, he is instructed to train in max 100% of the average intensity, or max 100% of the average training time. In case the female user has low temperature, she is instructed to train in max 125% of the average intensity, or max 125% of the average training time. If the male user has low temperature, he is instructed to train in max 125% of the average intensity, or max 125% of the average training time. The supplemental rules which can be implemented in an example, may be as follows in a form of an age rule:

In case the user age is less than 55 years, the table of FIG. 4 is applied as such.

In case the user age is more or equal than 55 years but less than 65 years, the table of FIG. 4 is applied with 10% reductions to the presented values.

In case the user age is more or equal than 65 years, the table of FIG. 4 is applied with 20% reductions to the presented values.

Importantly, the number of consecutive nights in the highest temperature quartile (or any other predefined percentile) can further affect training guidance by lowering the recommended intensity and/or volume or other aspects of training guidance. Further on, after recovering from high temperature values, the number of days when temperature has been normalized can further give rise to higher intensity and/or volume recommendation. Further on, there can be a threshold value, e.g. three normal temperature days are required before high intensity is recommended.

In more detail relating to the above, in a preferable example, the number of days how long the temperature has been higher than normative value, is taken into account in training instructions. In an example, instead of average, the normative value can be around $25^{th}$ percentile for women and around $50^{th}$ percentile for men (to represent a typical follicular phase temperature for women). This can be done with or without determining the actual ovulation time point or start day of the period, and subsequently, it could also work for men. Also, in another example, the number of days how long the temperature has been normal i.e. within a reasonable range (such as ±0.3° C.) from the normative value (average or e.g. $30^{th}$ percentile) is taken into account. For example, training recommendation can be determined to be high only at the $3^{rd}$ day after the temperature has normalized after being high, or the training recommendation becomes normal only after 3 consecutive nights with a slightly elevated temperature. In a preferably example, a clearly elevated temperature leads to a "no exercise" or "light exercise" recommendation. Of course, some more age gaps or ranges can be determined, and not just gender but some other personal characteristics, such as a cardiovascular fitness or physical condition level of the user, can be taken into account as well in determining these supplemental rules.

Figure 5:
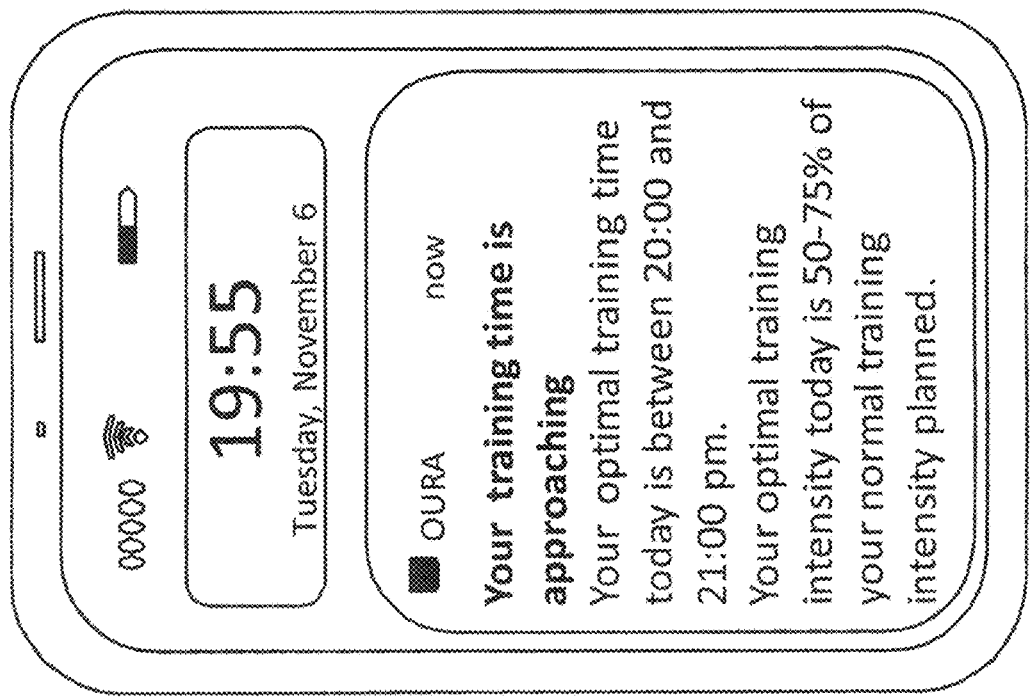
FIG. 5 is an illustration of exemplary training guides on the display of a mobile device, in accordance with aspects of the present disclosure.

FIG. 5 illustrates an example on how the personal smartphone of the user might inform the user on the incoming training session. The exemplary date and time is here 6 November (Tue) at 19:55 (7:55 PM). The algorithm may formulate the determined training instructions to the smartphone screen as:

"Your training time is approaching. Your optimal training time today is between 20:00 and 21:00 PM. Your optimal training intensity today is 50-75% of your normal training intensity planned."

This piece of instructions is given five minutes before the start of the optimal training session time range, but this is merely an example. If it can be assumed that the user is at home, and the training should most likely be performed at a gym, then the "warning" i.e. the training instructions can be given to the user e.g. 30-60 minutes before the optimal training session's start time.

In other words, the algorithm is giving an alert to the user for a start of the training and/or for receiving the training instructions.

Figure 6:
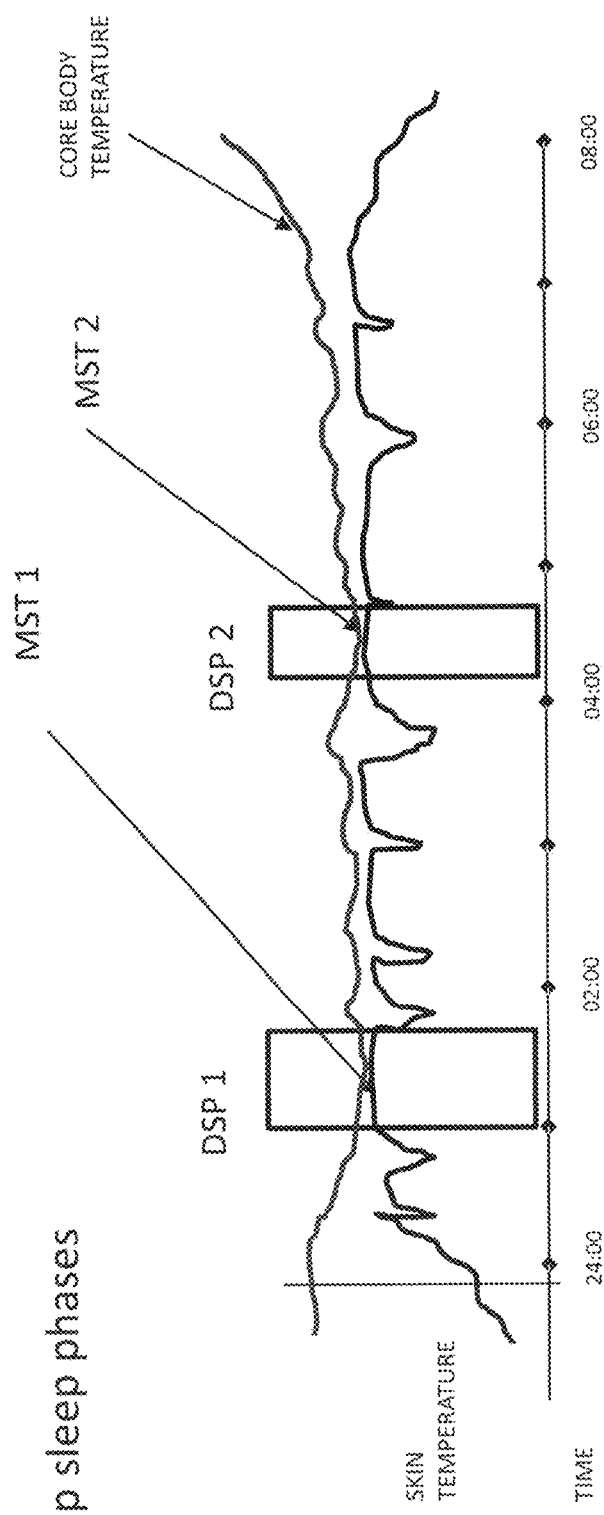
FIG. 6A is an illustration of a measured skin temperature at night for determining an optimum daily temperature value for each night, in accordance with aspects of the present disclosure.
FIG. 6B is an illustration of a measured skin temperature at night for determining an optimum daily temperature value, in accordance with aspects of the present disclosure.
Figure 6:
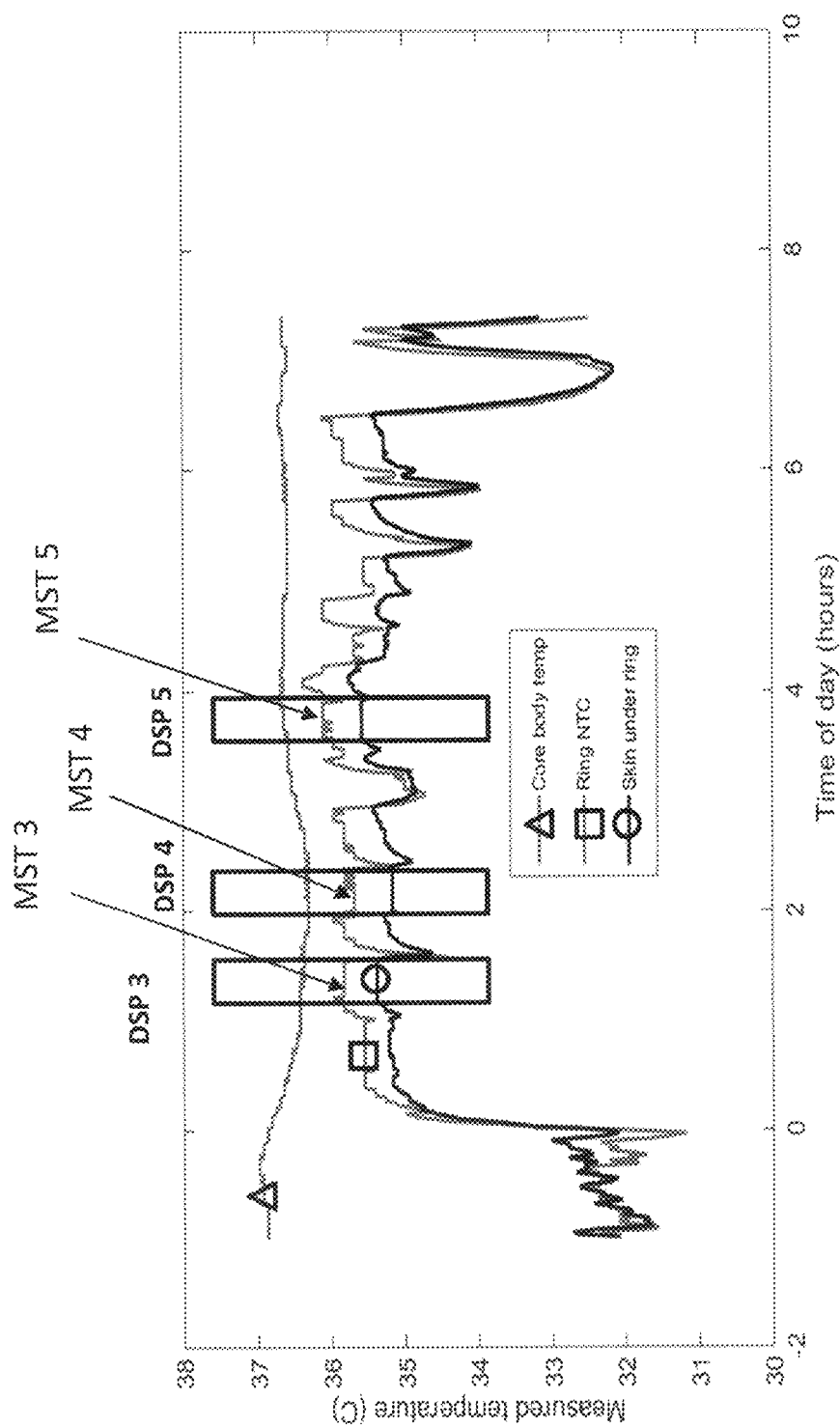

FIG. 6A is an illustration of a measured skin temperature at night for determining an optimum daily temperature value for each night, in accordance with an example of the present disclosure. FIG. 6B is an illustration of a measured skin temperature at night for determining an optimum daily temperature value, in accordance with an example of the present disclosure. It can be seen that highest temperatures measured from the finger are the closest to core body temperature curve. The abbreviations in FIGS. 6A and 6B are defined as "DSP M"=Deep or other sleep phase no. M; and "MST N"=Maximum skin temperature at phase N or representing an averaged or filtered maximum skin temperature at phase N. Now after this exemplary night has been measured, and the skin temperatures of the user during the night look as in FIG. 6A, we can define the two most relevant deep sleep phases during the night as from 01:00 to 01:35 AM (as DSP 1), and from 04:10 to 04:40 AM (as DSP 2). At these times skin temperature is estimated to be close to the core body temperature: In normal ambient temperature when the subject is in bed, skin temperature is always cooler than core body temperature. When human body has a need to cool down, periphery is opened by vasodilation and skin temperature gets warmer, and also close to the core body temperature.

It is also possible to define non-REM sleep phases such as light or deep sleep phases for determining an optimum daily temperature value for the user, in an example. Further it is possible to use the both light and deep sleep phases for determining an optimum daily temperature value for the user, in an example. The algorithm may also define other sleep periods to be used as sleep phases for determining an optimum daily temperature value for the user. The algorithm may for example define such a sleep phase based on HR, finding the time period during which the mean heart rate is low and most stable, and the time period can, for example, be between 10-60 minutes. The algorithm can use one or more parameters from the group of HR, activity and skin temperature, as in FIG. 3 and in FIG. 2, in an example.

In another example, the sleep phase definition can be based on heart rate and/or pulse waveform data to obtain best time windows for estimation of core body temperature, or basal body temperature. For example, restful, warm times when the HR is lowest, may represent a best phase for determining the skin temperature. This means a lowest activity period measured by an accelerometer in a device, and a highest temperature measured by a temperature sensor in a device for a certain time period, such as e.g. 30 minutes or any time period between 10-60 minutes. The temperature representing basal body temperature for a single night can also be a weighted estimate $[sum(W_i*T_i)/sum(W_i)]$ where $W_i$ is a weight applied to a period of time (such as 10-30 min) and $T_i$ is the corresponding skin temperature. $W_i$ is relatively bigger when the skin temperature is more stable and higher, and when less movement is detected and also the heart rate is lower and more stable. Also morning hours (3-6 AM) can have bigger weight (W) because this time period in 24-h body clock is when the core body temperature is the lowest (hence it is called basal body temperature).

In any case, when a desired number of most relevant deep or other sleep phases or periods have been defined during the night, the algorithm determines the maximum skin temperature MST 1 during DSP 1 and the same for the other relevant sleep phases (here, MST 2 during DSP 2). In this example, there are two relevant deep sleep phases. In an example of the present disclosure, the algorithm determines the maximum skin temperature as a mean value of all MSTs. In case of only a single relevant deep sleep phase, the MST is the same as MST 1. In the case of the depicted example, the calculation would be:

$$MST=(MST1+MST2)/2 \tag{1}$$

After this, the value of MST (maximum skin temperature) is entered into the selection process of an appropriate training instruction for that specific day.

The calculation process is repeated for the next night separately, and then a new MST is obtained for the next day, and for updated training instructions for that day.

In another example, the MST for the day could be determined as the absolute maximum of the obtained skin temperatures during all the deep sleep phases (thus, without the mean calculations).

FIG. 6B now illustrates another example comprising steps of a method for determining an optimum daily temperature value for the user. There are now three sleep periods defined and marked as DSP 3, DSP 4 and DSP 5. It can now be seen that there can be single higher temperature values and also noise in the temperature values during periods DSP 3, DSP 4 and DSP 5.

In this example, an algorithm for defining MST 3 (maximum skin temperature in DSP 3) is now filtering the temperature values. The filtering can be for example discarding the highest temperature value, and selecting the second highest temperature value during DSP 3 as MST 3. It is also possible that MST 3 is defined as a mean value of second and third temperature values during DSP 3 as MST 3. Thus, a single sharp temperature peak, which could represent an erroneous value, can be discarded during DSP 3 (and of course in any desired period).

MST 4 and MST 5 can be defined in a similar way as MST 3 or it can be further processed with a known method for defining a representative maximal value among values of certain successive measurement values. This can be, for example, selecting values whose magnitude varies from 80 to 90% and then taking a mean value of this sub-group.

Now the representative MST value for the night can be defined using MST 3, MST 4 and MST 5 similarly as for MST 1 and MST 2 above, as their average value. It is also possible to use other rules for defining the representative MST value for the night. For example, this can be done by selecting the minimum or maximum value among MST 3, MST 4 and MST 5. It is also possible to define the representative MST value for the night by filtering out the maximum or minimum value of MST 3, MST 4 and MST 5 and take the average value of the remaining two values.

Figure 7:
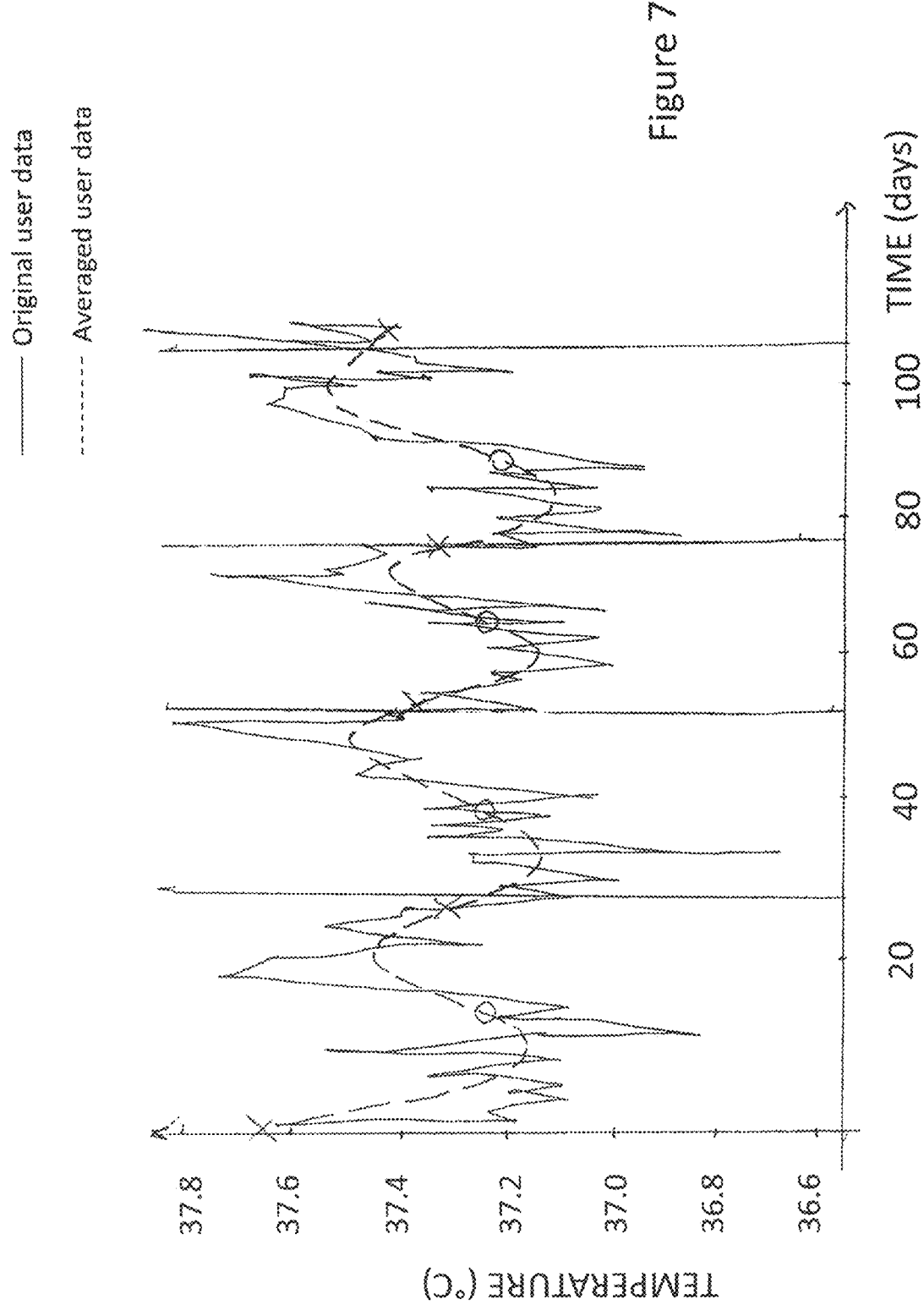
FIG. 7 is an illustration of a temperature curve based on the daily temperature values, in accordance with aspects of the present disclosure.

FIG. 7 illustrates an example, where a temperature curve is determined based on the nightly temperature values i.e. MSTs over multiple days, e.g. over 10-120 days. In that exemplary temperature measurement graph obtained from real user data, the more noisy looking graph (shown with a continuous line) is representing the actual estimated core body temperature data (based on nightly skin temperatures of the user), as one value per day (actually, night), and calculated according to a selected example presented above in connection to FIG. 6. It can be seen that the minimum skin temperatures in the exemplary period of 110 days can vary a lot; here from +36.7° C. to +37.8° C.

In a second step here, the algorithm may determine a second curve which here resembles a bit like sinusoidal curve. In this example, the second curve is determined from the successive MST values (one for each day), by e.g. taking a moving average of 2, 3 or 4 or 5 successive samples. The curve may have a cycle length of 10-45 days, mostly 23-35 days, and averagely 28 days. Then the result may look like the oscillating, sinusoidal-like graph of FIG. 7 (shown in dashed line). From this piece of information, certain temperature trends can be seen (although smoothened). With X:s, there have been marked some time instants when the temperature decreasing trend is at its maximum (i.e. mathematically, the curve's derivative is at its minimum). This downward trend at the estimated core body temperatures can be used in determining a proper and most reasonable training instruction for that user in that particular time, in an example. Also, FIG. 7 marks four circles, which represent time instants when the increasing of the averaged core body temperature has reached its usual maximum speed. In other words, the circles show the time instants when the linearly increasing slope starts for the temperature value shown in dashed line. This information can also be used in determining a reasonable training instruction for the respective user in a desired time instant.

Figure 8:
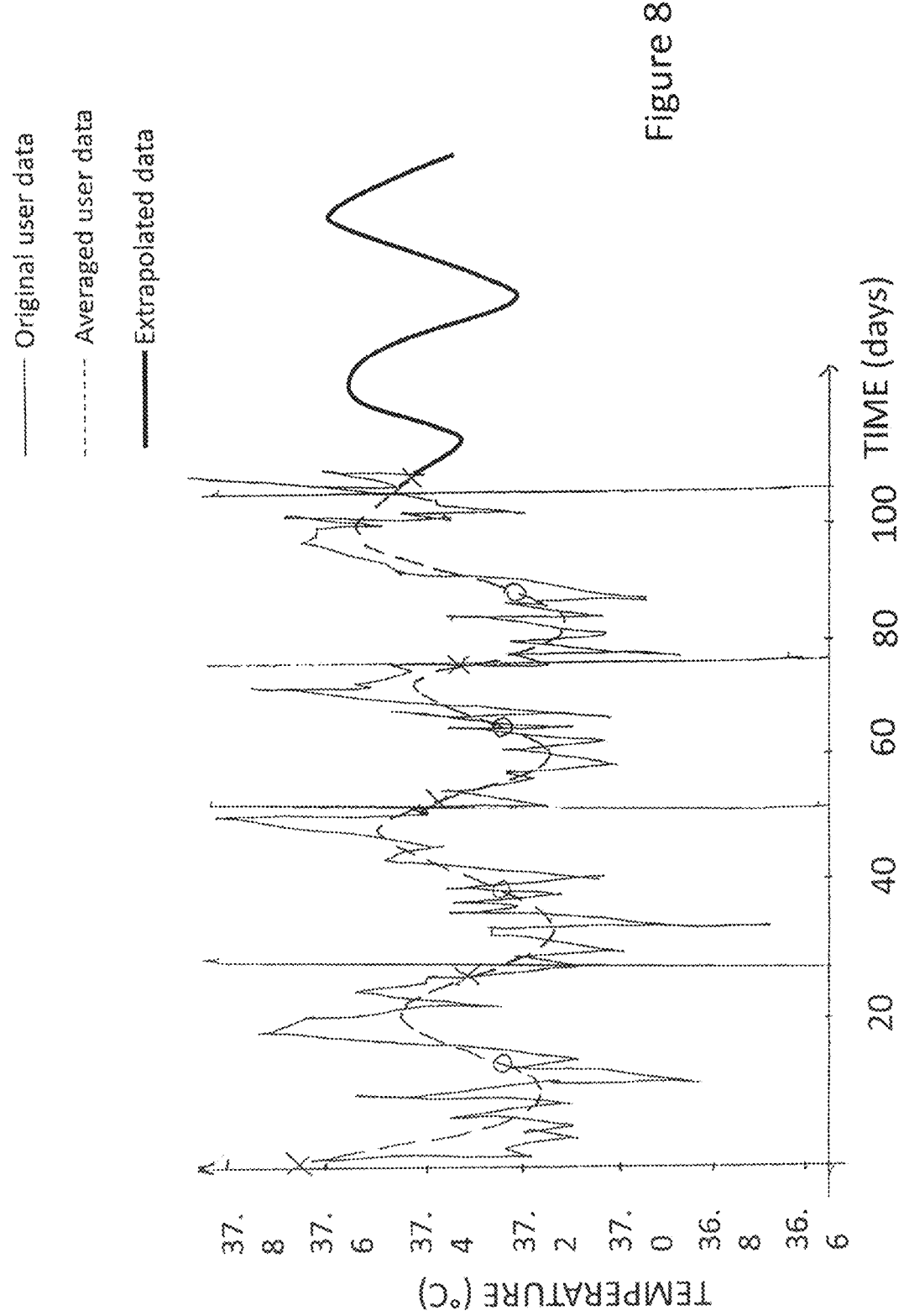
FIG. 8 is an illustration of a temperature curve and estimated values for the future based on the daily temperature values, in accordance with aspects of the present disclosure.

FIG. 8 now illustrates the same curves as FIG. 7 (with X:s and circles) but with an added extrapolated section shown with a thicker, continuous line in the right side of FIG. 8. This means that by using the known pattern in the estimated core body temperatures oscillations, we can forecast the future behavior of the core body temperature. This extrapolated, i.e. forecast section is just marked by hand in FIG. 8 for illustrative purposes. In other words, we may forecast the core body temperature values for a number of future days, if there is a recognizable pattern, e.g. in a form of oscillations based either of female menstrual cycles, or training habits, or other personal traits or activities made by the user. Even the time of the year (winter/summer) may have an effect on the core body temperature, if the user is prone e.g. to create inflammatory situation or even illness during a certain part of the year, or after a certain type of training. Some or all of these kinds of parameters may be used in forecasting the future core body temperature values. The forecasted values may be used in determining a proper training instruction for the user, merely as such or with some other previously defined parameter. Especially, this example is useful for giving a longer term training instructions for the user into the future, which do not cover only the next 24 hours. For example, if today is 23 November, the algorithm may determine training instructions for 30 November, and pre-inform them to the user today, and maybe a second time in the morning of 30 November Many alternative determination and information giving options are possible within the present disclosure.

In other words, in the determination of the day-to-day temperature cycle, the temperature curve is further extrapolated by estimating the temperature for the following days; and using the estimated temperature values for the training instructions and/or for training planning instructions for the future.

Figure 9:
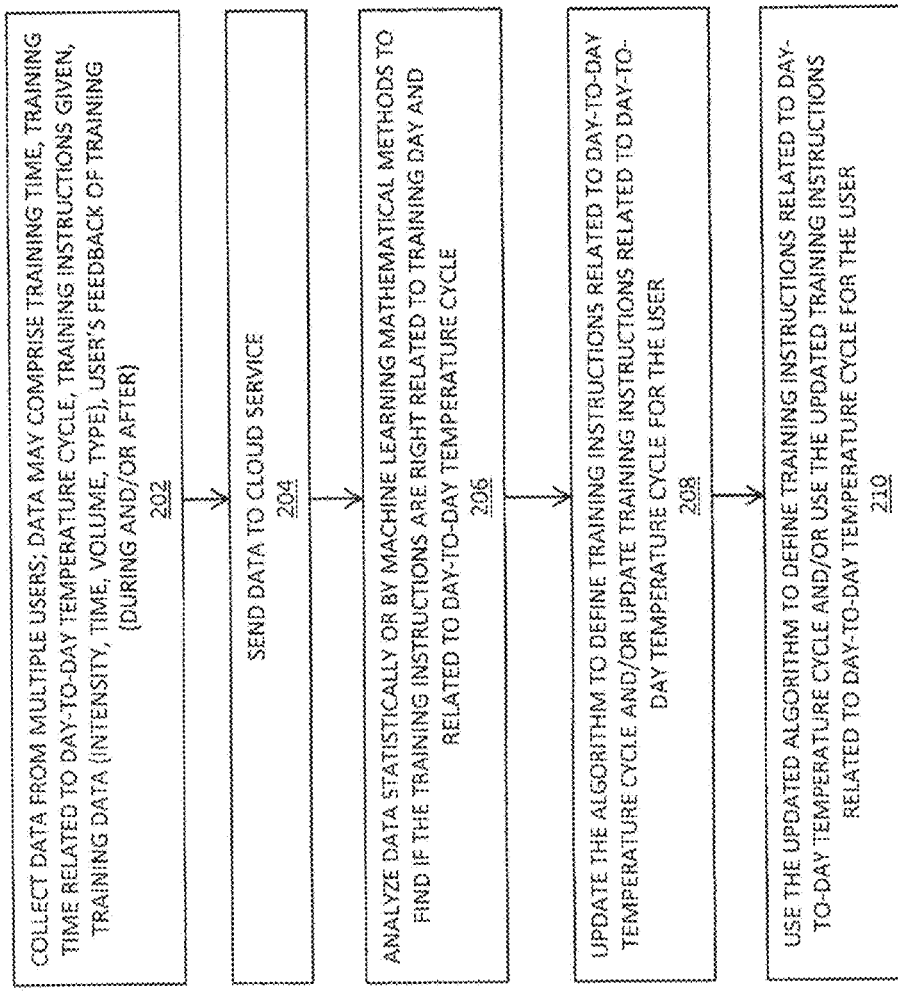
FIG. 9 is an illustration of a flow chart showing a method for collecting feedback from multiple users, in accordance with aspects of the present disclosure.

FIG. 9 illustrates steps of an example, where feedback is collected from multiple users. In this example, the algorithm collects feedback from the user based on the measured activity during the training time and a personal feedback about a feeling during and/or after the training. The feedback collection may be performed for larger group of users, and such data can be used in the determination of the training instructions for a single user. The database may comprise information from a long period of time from a large group of users, and this database may be a cognitive database, i.e. it is updated all the time when the system is running. Thus, the training instruction quality is expected to rise, and the feedback should get even better over time. And in case the feedback would get to a lower score, the system may take this into account by making a larger change for the proposed training instructions.

Furthermore, in an example, the algorithm may modify the training instructions based on the collected feedback from multiple users based on the measured activity during the training time and the personal feedback about the feeling during and/or after the training, and the relation of the related latest temperature value to the temperature cycle.

In other words, using the wordings of the flow chart of FIG. 9, at first step 202, the method collects data from multiple users; where the data may comprise training time, training time related to day-to-day temperature cycle, training instructions given, training data (intensity, time, volume, type), user's feedback of training (during and/or after). At the second step 204, the data is sent to cloud service. At the third step 206, the method analyses data statistically or by machine learning mathematical methods to find if the training instructions are right related to training day and related to day-to-day temperature cycle. At the fourth step 208, the algorithm is updated to define training instructions related to day-to-day temperature cycle and/or update training instructions related to day-to-day temperature cycle for the user. At the fifth and final step 210, the updated algorithm is used to define training instructions related to day-to-day temperature cycle and/or use the updated training instructions related to day-to-day temperature cycle for the user.

Figure 10:
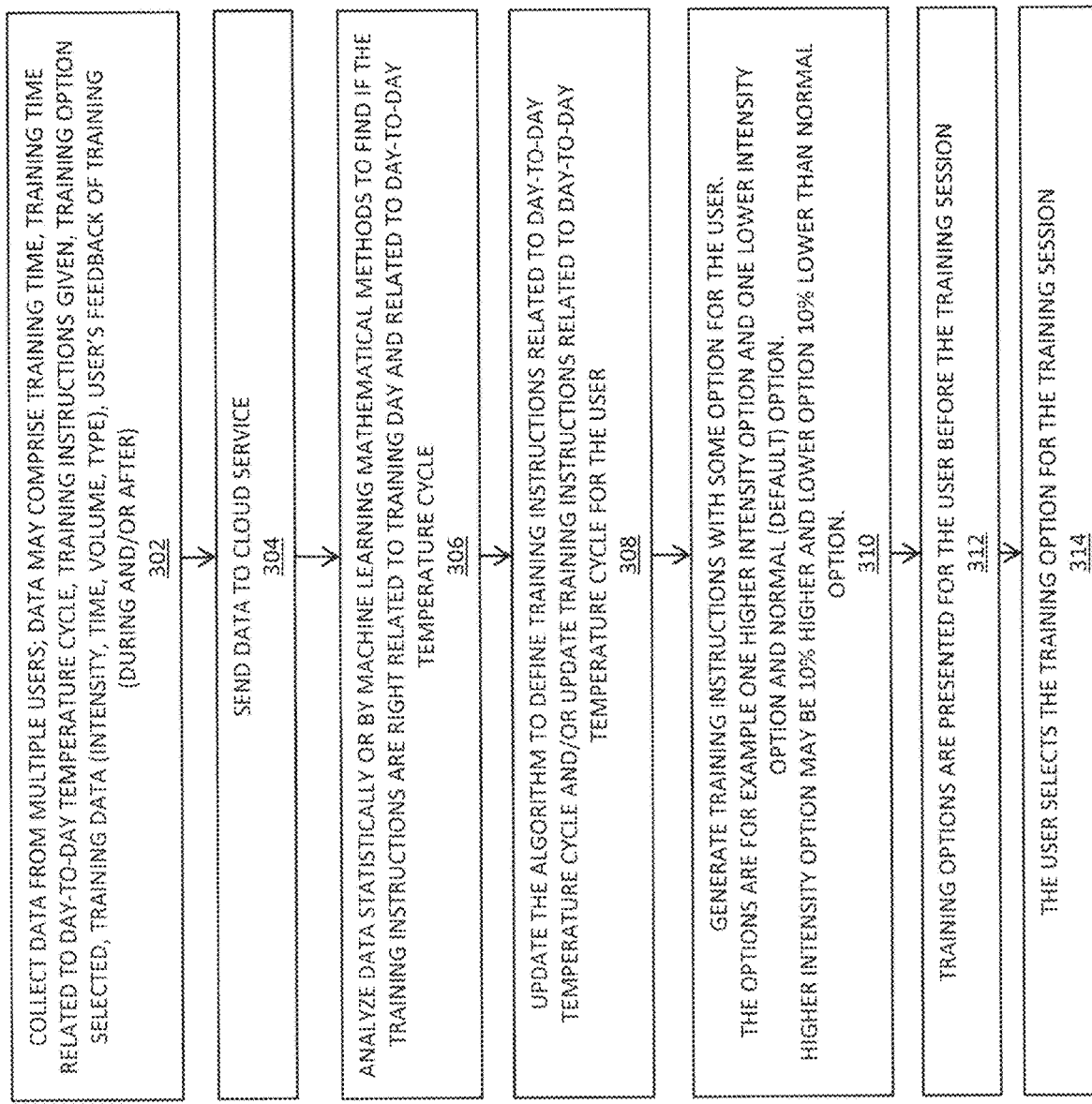
FIG. 10 is an illustration of a flow chart showing a method for collecting feedback from multiple users and optimizing general training instructions or training instruction options, in accordance with aspects of the present disclosure.

FIG. 10 illustrates steps of an example, where feedback has been collected from multiple users, and general training instructions are optimized for the user, or several training instructions options are provided to the user for him/her to select from. In more detail, at the first step 302 of this method, it collects data from multiple users; data may comprise training time, training time related to day-to-day temperature cycle, training instructions given, training option selected, training data (intensity, time, volume, type), user's feedback of training (during and/or after). At the second step 304 of this method, data is sent to cloud service. At the third step 306 of this method, it analyses data statistically or by machine learning mathematical methods to find if the training instructions are right related to training day and related to day-to-day temperature cycle. At the fourth step 308 of this method, the algorithm is updated to define training instructions related to day-to-day temperature cycle and/or update training instructions related to day-to-day temperature cycle for the user. At the fifth step 310 of this method, it generates training instructions with some option for the user. The options are for example one higher intensity option and one lower intensity option and normal (default) option. The higher intensity option may be 10% higher and the lower intensity option 10% lower than the normal option. At the sixth step 312 of this method, training options are presented for the user before the training session. Finally, at the seventh step 314 of this method, the user selects the training option for the training session.

Figure 11:
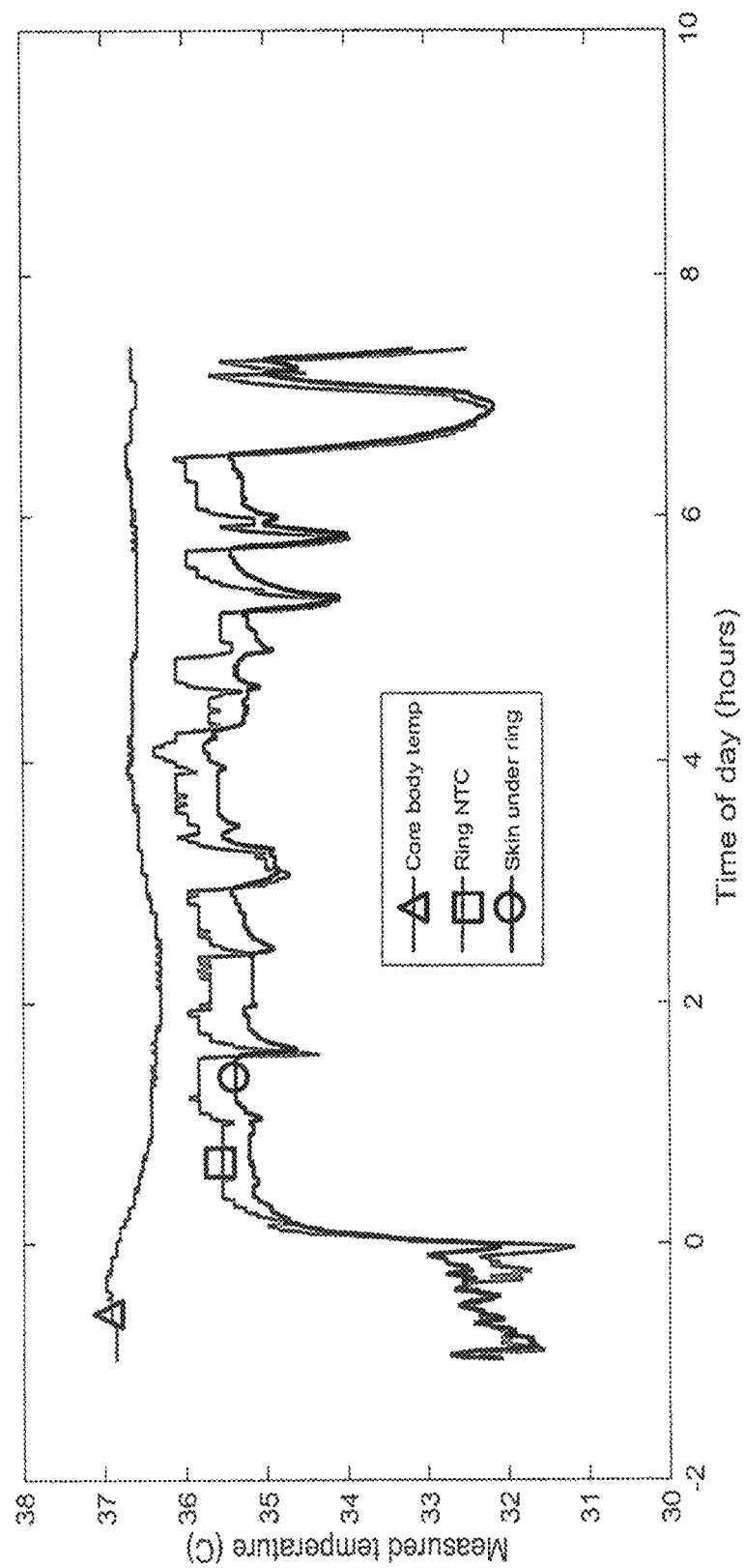
FIG. 11 illustrates a graph depicting the relationship between the core (i.e. basal) body temperature and the skin temperature, in accordance with aspects of the present disclosure.

FIG. 11 illustrates a graph depicting the relationship between the core (i.e. basal) body temperature and the skin temperature, in an example of the present disclosure. The uppermost curve is the core body temperature, locating usually between +36 and 37° C. The curve locating mostly in the middle is the "Ring NTC" which means the temperature which the ring-type of a wearable measuring device senses from a finger of the user. Then the actual skin temperature of the finger which wears the ring, and measured under the worn ring, is shown as the curve mostly locating as the lowermost one. We can see that the core body temperature is quite stable but the skin temperature varies a lot; in this example from 31.7° C. to 35.8° C. The temperature sensed by the ring follows pretty closely the actual skin temperature but still there are some differences, although it can be assumed that the ring will be constantly in good contact with the user's finger. There is still "an interface" between the metallic or other type of the wearable ring and the human skin, which is not 100% perfect for conducting heat. The maximum difference between the ring sensor temperature and the actual skin temperature seems to be a little less than 1 degrees. It is also known that there are temporal changes which can change the skin temperature and temperature measured under the ring (ring NTC) and their relationship. Such changes can be originated due to a rapid change of room temperature, due to the fact that the user is covering the ring, finger or hand by a blanket or a pillow. NTC calibration may also be biased, but like other systematic issues, this is removed by using user's own history as the reference/baseline/source for percentile based limits.

Figure 12:
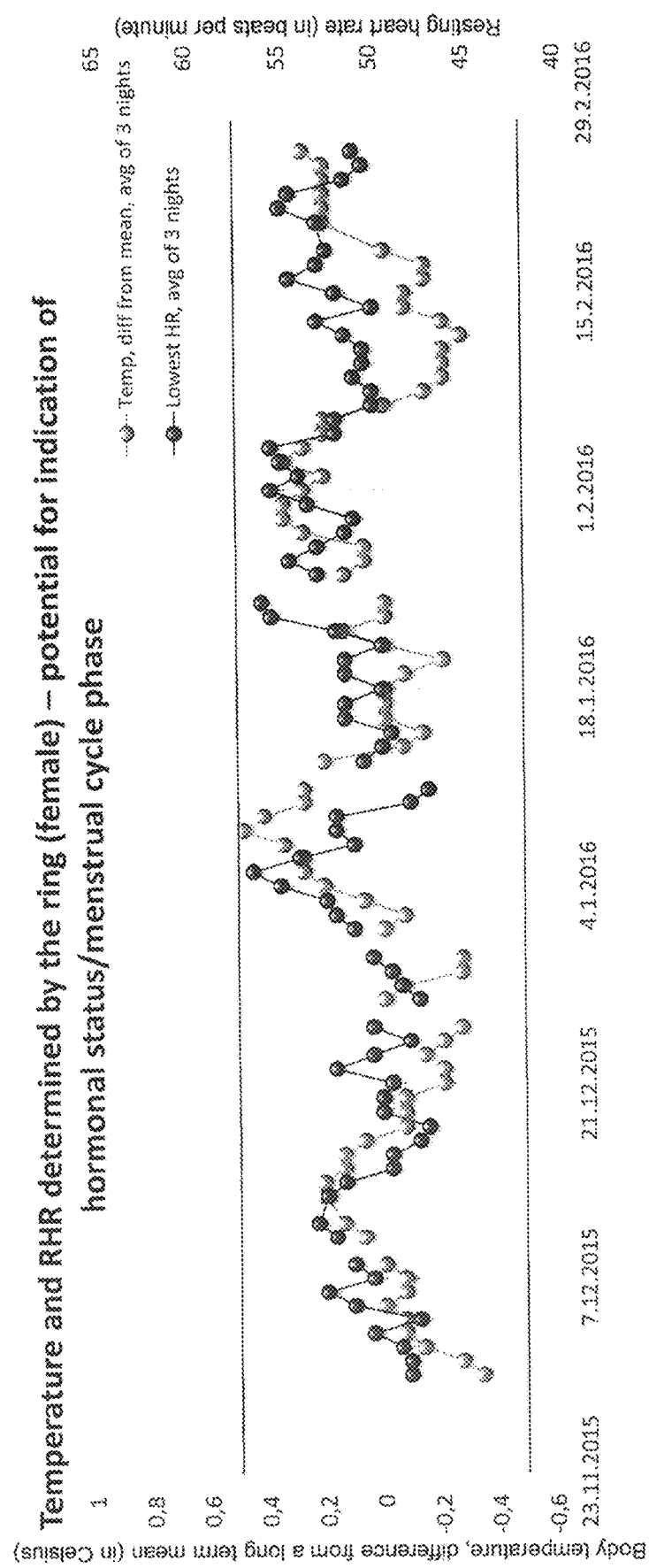
FIG. 12 illustrates two graphs showing a female body temperature difference from a long term mean value, and heart rate in the rest, in accordance with aspects of the present disclosure.

FIG. 12 illustrates two graphs showing a female body temperature difference from a long term mean value, and heart rate in the rest, in an example of the present disclosure. In pre-menopausal women, or women in general, temperature is also reflecting a monthly hormonal rhythm. The lighter dots represent the body temperature difference from a long term mean value in degrees Celsius, averaged from three successive nights. The darker dots represent the lowest, i.e. resting heart rate (marked as RHR), averaged from three successive nights, in beats per minute (bpm). These curves enable the indication of the hormonal status or menstrual cycle phase of the female user and this information may be used in determining a proper training instruction for the female user, in part or in full, in an example of the present disclosure.

Figure 13:
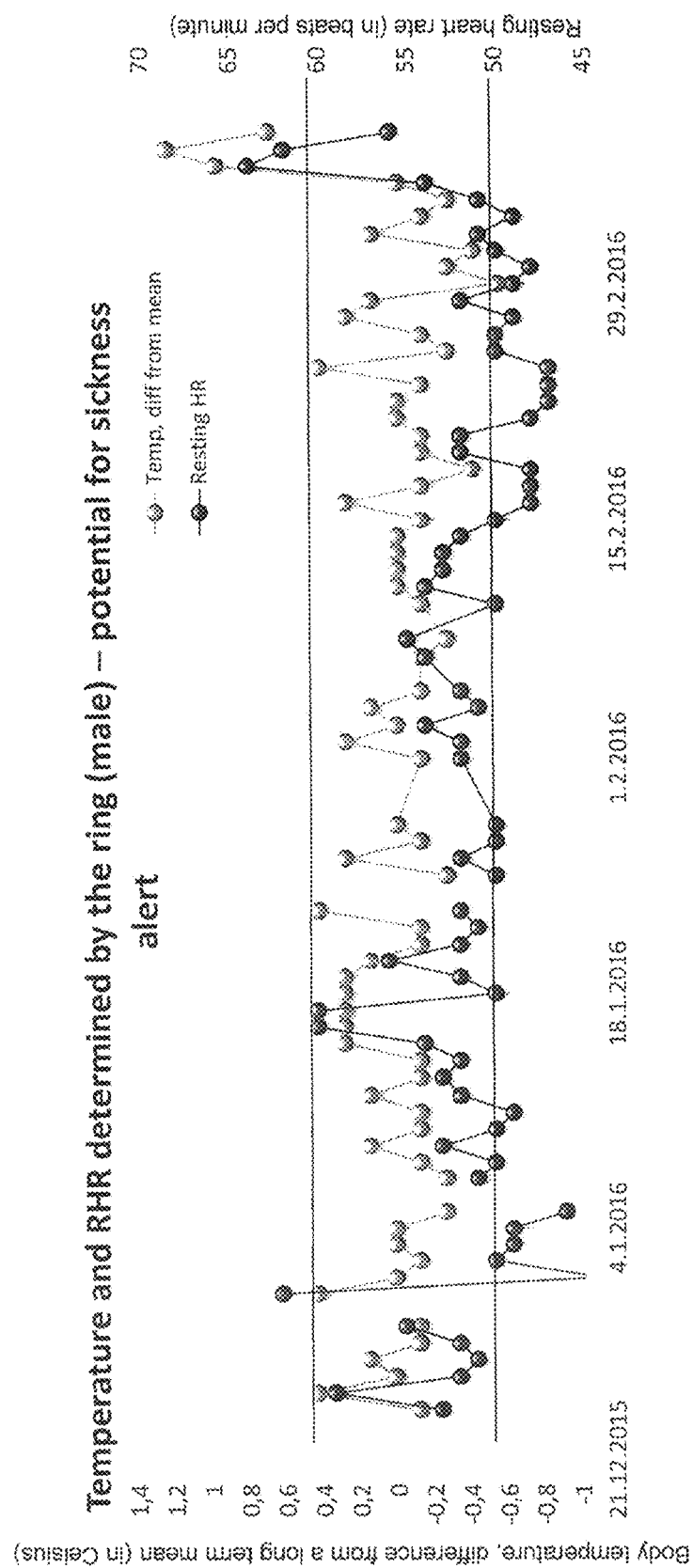
FIG. 13 illustrates two graphs showing a male body temperature difference from a long term mean value, and heart rate in the rest, in accordance with aspects of the present disclosure.

FIG. 13 illustrates two graphs showing a male body temperature difference from a long term mean value, and heart rate in the rest, in an example of the present disclosure. A male test person was actually able to explain almost all variability in data with changes in the amount of his training, in the time of the training, or whether being sick or whether during or after some alcohol use. Among the first users, we have received a lot of feedback on how essential are the resting heart rate and the body temperature as parameters. The lighter dots represent the body temperature difference from a long term mean value in degrees Celsius. The darker dots represent the lowest, i.e. resting heart rate (marked as RHR), in beats per minute (bpm). Thus, this example comprises no averaging. These curves enable the indication of a possible illness (i.e. sickness) of the male user and this information may be used in determining a proper training instruction for the male user, in part or in full, in an example of the present disclosure.

Generally, when the training instructions are provided, they may comprise an amount of training, a type of training, a duration of training, an intensity of training, a time during the day for the training to take place, and/or a guidance to stretch or rest.

In general, training information (and/or alerts in this sense) can be given via a smartphone application to the user.

As an advantage of the present disclosure, when concerning a lot of data obtainable from various user measurement devices, rings are much more reliable data sources than wrist devices, because the physical contact between the ring and the finger skin is usually very good during the day and night, and usually the ring can remain in its place always, like a wedding ring. For wrist devices, it's much easier to be removed or "forgotten" somewhere. Furthermore, the wrist devices' physical contact to the wrist skin is not usually that good, and the tightness preferences within different users vary a lot with the wrist devices, such as with the wrist watches. Therefore, ring devices as wearable devices are very good in the concept of the present disclosure.

The present disclosure is not merely restricted to the examples disclosed above but the present disclosure may vary within the scope of the claims.

What is claimed is:

1. A method for providing training instructions to a user, comprising:
   collecting a set of information related to the user comprising an age and a first gender;
   receiving a set of measurement data related to the user comprising a measured skin temperature obtained by one or more sensors of a wearable ring device worn by the user;
   determining a representative temperature value for at least one time period, wherein the at least one time period is a pre-selectable parameter, wherein the representative temperature value is measured during a time that the user is asleep;
   determining a day-to-day temperature cycle based on successive representative temperature values for the at least one time period;
   determining training instructions for a current day based on at least a latest temperature value, the first gender, and a relationship between the latest temperature value and the day-to-day temperature cycle, wherein the training instructions are different from second training instructions for a second gender that is different from the first gender; and
   generating a signal to display the training instructions to the user via a user interface.

2. The method of claim 1, wherein the at least one time period is selected from values of 12 hours or 24 hours.

3. The method of claim 1, wherein the relationship comprises at least qualitative values of high, middle, and low.

4. The method of claim 1, further comprising:
   measuring a skin temperature of the user by a temperature sensor comprised in the wearable ring device, wherein the wearable ring device locates adjacently and in contact or in immediate proximity with the user's skin.

5. The method of claim 1, wherein the time that the user is asleep is a predetermined time period in the night.

6. The method of claim 1, wherein determining the representative temperature value comprises:
selecting a maximum skin temperature within a defined time window during one or more defined sleeping periods, where the maximum skin temperature is an averaged value over a period of 10-30 minutes.

7. The method of claim 6, wherein the one or more defined sleeping periods comprise non-rapid eye movement (NREM) sleep, the method further comprising:
selecting a median value, a minimum value, a a maximum value, or an average value of temperature values of NREM sleep phases in case there are multiple NREM sleep periods in the time that the user is asleep.

8. The method of claim 1, wherein determining the day-to-day temperature cycle is based on successive temperature values.

9. The method of claim 8, further comprising:
selecting the successive temperature values once a day; and
using a moving average of three, four or five previously obtained, successive temperature values.

10. The method of claim 1, further comprising:
selecting training instructions for the current day based on the latest temperature value obtained either today or yesterday, so that:
if the latest temperature value is higher than average, the selected training instructions comprise a lower intensity exercise or a longer lasting exercise, and
if the latest temperature value is lower than average, the selected training instructions comprise a higher intensity exercise or a shorter lasting exercise or stretching or rest instead of training.

11. The method of claim 1, wherein, in the determination of the day-to-day temperature cycle, the day-to-day temperature cycle is further extrapolated by estimating one or more temperature values for one or more following days, the method further comprising:
using the estimated one or more temperature values for the training instructions or for planning future training instructions.

12. The method of claim 1, further comprising:
providing the training instructions comprising an amount of training, a type of training, a duration of training, an intensity of training, a time during the day for the training to take place, or a guidance to stretch or rest.

13. The method of claim 1, further comprising:
giving an alert to the user for a start of the training or for receiving the training instructions.

14. The method of claim 1, further comprising:
measuring activity of the user during a training time; and
determining if the user has performed the training as instructed.

15. The method of claim 14, further comprising:
collecting feedback from the user based on the measured activity during the training time and a personal feedback about a feeling during or after the training.

16. The method of claim 15, further comprising:
modifying the training instructions based on collected feedback from multiple users, the measured activity during the training time, the personal feedback about the feeling during or after the training, and the relationship between the related latest temperature value to the temperature cycle.

17. A system for providing training instructions to a user, comprising:
a computer;
a personal smartphone;
a wearable ring device worn by the user; wherein the system is configured to:
collect, by the smartphone, a set of information related to the user comprising an age and a first gender;
receive a set of measurement data related to the user comprising a measured skin temperature obtained by one or more sensors of the wearable ring device;
determine a representative temperature value for at least one time period, where the time period is a pre-selectable parameter, either in the smartphone or in the computer, wherein the representative temperature is measured during a time that the user is asleep;
determine a day-to-day temperature cycle based on successive representative temperature values for the at least one time period, either in the wearable device, in the smartphone or in the computer;
determine training instructions for a current day based on at least a latest temperature value, the first gender, and a relationship between the latest temperature value and the temperature cycle, wherein the training instructions are different from second training instructions for a second gender that is different from the first gender, either in the smartphone or in the computer; and
generate a signal to display the training instructions to the user via a user interface of the smartphone.

18. A non-transitory computer-readable medium storing code for providing training instructions to a user, the code comprising instructions executable by a processor to:
collect a set of information related to the user comprising an age and a first gender;
receive a set of measurement data related to the user comprising a measured skin temperature obtained by one or more sensors of a wearable ring device worn by the user;
determine a representative temperature value for at least one time period, where the time period is a pre-selectable parameter, wherein the representative temperature is measured during a time that the user is asleep;
determine a day-to-day temperature cycle based on successive representative temperature values for the at least one time period;
determine training instructions for a current day based on at least a latest temperature value, the first gender, and a relationship between the latest temperature value and the temperature cycle, wherein the training instructions are different from second training instructions for a second gender that is different from the first gender; and
generate a signal to display the training instructions to the user via a user interface.

* * * * *